| United States Patent [19] | [11] | 4,128,665 |
|---|---|---|
| Hunt et al. | [45] | Dec. 5, 1978 |

[54] SUBSTITUTED DINITROTRIFLUOROMETHYLDIPHENYLAMINE AND PESTICIDAL COMPOSITIONS CONTAINING SAME

[75] Inventors: John D. Hunt, Wokingham; Frederick C. Peacock, Ascot, both of England

[73] Assignee: Imperial Chemical Industries Limited, London, England

[21] Appl. No.: 627,771

[22] Filed: Oct. 28, 1975

[30] Foreign Application Priority Data

Nov. 6, 1974 [GB] United Kingdom ............... 47977/74

[51] Int. Cl.$^2$ .......................... C07C 87/54; A01N 9/20
[52] U.S. Cl. ................................. 424/330; 260/465 E; 260/571; 260/576; 424/304
[58] Field of Search .......................... 260/576; 424/330

[56] References Cited

U.S. PATENT DOCUMENTS

| 2,212,825 | 8/1940 | Daudt et al. ...................... 260/576 X |
| 3,227,758 | 1/1966 | Richter et al. ...................... 424/330 |
| 3,493,662 | 2/1970 | Duerr ...................... 424/330 |
| 3,562,332 | 2/1971 | Schmidt et al. ...................... 260/576 |
| 3,950,377 | 4/1976 | Barlow ...................... 260/576 X |

FOREIGN PATENT DOCUMENTS

654690 12/1962 Canada ...................... 260/576

*Primary Examiner*—Winston A. Douglas
*Assistant Examiner*—John J. Doll
*Attorney, Agent, or Firm*—Cushman, Darby & Cushman

[57] ABSTRACT

2,5'-Bistrifluoromethyl-2'-chloro-4,6-dinitrodiphenylamine and pesticidal compositions containing the same as active ingredient.

6 Claims, No Drawings

SUBSTITUTED DINITROTRIFLUOROMETHYLDIPHENYLA- MINE AND PESTICIDAL COMPOSITIONS CONTAINING SAME

This invention relates to a novel diphenylamine derivative, to a method of preparing it, to compositions comprising it and to methods of combating pests using it; more particularly to methods of combating insect, acarine and fungal pests of plants.

In prior U.S. application Ser. No. 556,421, there are described diphenylamine derivatives of the formula:

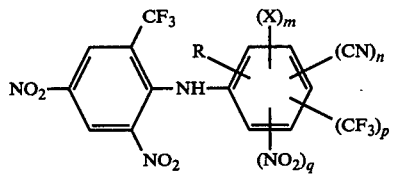

wherein R represents hydrogen or an alkyl or alkoxy group containing up to six carbon atoms, X represents a halogen atom, m is zero or an integer from one to three, n is zero or one, p is zero, one or two and q is zero, one or two, the sum of m, n, p and q being one, two or three; provided that the group

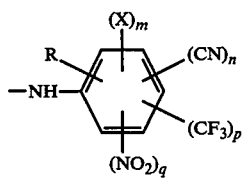

does not represent the 4-cyano-2,6-dinitroanilino group or the 4-trifluoromethyl-2,6-dinitroanilino group.

According to the present invention, we provide a further new diphenylamine derivative viz. 2,5'-bistrifluoromethyl-2'-chloro-4,6-dinitrodiphenylamine having the formula:

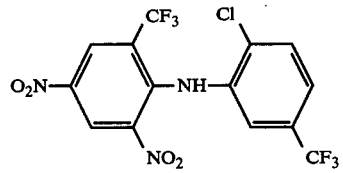

At the present time, for a chemical compound to be of special interest and of commercial success in the pesticide field it must possess many desirable properties. It must be sufficiently efficacious to interest the farmer, horticulturalist and manufacturer, and to possess toxicological properties acceptable to Government registration and environmental authorities.

Pesticidal compounds when applied to plants for non-herbicidal use, ideally, should cause no damage to the plant (i.e. be non-phytotoxic) or to the fruit of the plant e.g. should not produce russetting of apples. Whilst the chemical compound must be sufficiently persistent in its pesticidal activity to control the pest much importance is now given to chemical compounds which do not persist too long as to create residue problems in the field and on the crop of the plant. Selectivity of pesticidal action is another feature desirable of a chemical compound pesticide. Broad-spectrum pesticides which kill pests indiscriminately are under increasing attack from environmentalists. Chemical compounds which do not affect predators of pests are to be favoured.

The aforesaid mentioned prior application discloses a class of diphenylamines having insecticidal, acaricidal and fungicidal properties. No one compound of said application, which was exemplified and tested, was found to have such an aggregate of biological properties as that found in the compound of the invention. In view of the large number of compounds tested it is remarkable that a compound falling within this class should later emerge with such outstanding and acceptable biological properties. The aggregate of the properties of high efficaciousness, low level of phytotoxicity, persistence and acceptable mammalian toxicity singles out the compound of the invention as a true selection from the previous compounds.

According to a further feature of the invention we provide a process for the manufacture of the said diphenylamine derivative which comprises reacting a compound of the formula:

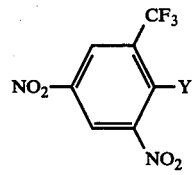

wherein Y represents a halogen atom; with a compound of formula:

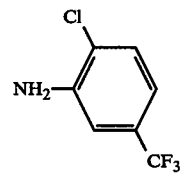

This process may in some cases be carried out by heating the reactants together in the absence of a diluent, and/or base, but preferably a non-reacting solvent or diluent and a base is present. Suitable solvents include, for example, non-hydroxylic materials such as dimethylformamide, dimethylsulphoxide, sulpholane, acetonitrile, and tetrahydrofuran. Of these dimethylformamide is particularly preferred. Hydroxylated solvents, for example, methanol and ethanol, may be used in certain circumstances when the presence of the hydroxyl group does not interfere with the progress of the reaction. Suitable bases include sodium hydride (although not when a hydroxylated solvent or diluent is used), alkali metal carbonates, such as sodium carbonate and alkali metal hydroxides such as potassium hydroxide. The temperature at which the reaction may be carried out will depend upon the choice of reactants, solvent or diluent and base. When dimethylformamide and sodium hydride are used the reaction generably takes place in the range −10° C. to +30° C., but higher temperatures up to 100° C. may be employed when other bases are used.

The process generally consists of dissolving or suspending the reactant bearing the amino group in a solvent or diluent in the presence of the base, allowing the base to react with the reactant by the removal of a proton from the amino group, and thereafter adding the second reactant. After allowing a period of time for the reaction to occur the product may be isolated by dilution with a diluent in which the product is insoluble, usually water, which causes the product to precipitate out. The product may then be separated by filtration and recrystallised from a suitable recrystallising solvent or mixture of solvents to yield the product in a substantially pure state.

As stated above, the diphenylamine derivative of the invention possesses useful insecticidal properties and useful fungicidal properties. In particular it may be used to combat and control phytophagous mites, which are pests of apples and pears, amongst other crops. The invention compound has been found to be more effective than "PLICTRAN" and "KELTHANE", which are both recommended in the control of phytophagous mites. "PLICTRAN" and "KELTHANE" are Trade Marks.

In another particular aspect the invention compound gives control of aphids; an important pests of many crops in many parts of the world. In tests against both aphid and phytophagous mite pests the invention compound was superior, where efficaciousness, phytotoxicity and mammalian toxicity were considered together, to the compounds of the class described in the aforementioned U.S. application Ser. No. 556,421. Many of the compounds of U.S. application Ser. No. 556,421 which are more effective than the compound of the invention in the control of the above mentioned pests are more toxic to mammals or more phytotoxic to the host plant.

The invention also includes pesticidal compositions comprising the diphenylamine derivative of the invention and also comprising a diluent or carrier.

In a further aspect, therefore, this invention provides a pesticidal composition comprising as an active ingredient the diphenylamine of the formula:

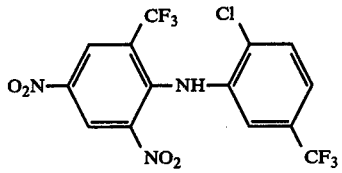

and a carrier for the active ingredient.

The diphenylamine derivative of this invention is preferably used in the form of compositions and these compositions may be used for agricultural and horticultural purposes. The type of composition used in any instance will depend upon the particular purpose for which it is to be used.

The compositions may be in the form of dusting powders or granules wherein the active ingredient is mixed with a solid diluent or carrier. Suitable solid diluents or carriers may be, for example, kaolin, bentonite, kieselguhr, dolomite, calcium carbonate, talc, powdered magnesia, Fuller's earth, gypsum, diatomaceous earth and China clay. A suitable granular diluent is granulated pumice.

The compositions may also be in the form of dispersable powders or grains comprising, in addition to the active ingredient, a wetting agent, a dispersing agent, an emulsifying agent, a suspending agent, and a disintegrating agent to facilitate the dispersion of the powder or grains in liquids. Such powders or grains may include fillers and suspending agents. By the term "disintegrating agent" is meant a solid, readily water-soluble substance, e.g. a salt or a simple organic substance, which aids the disintegration of the dispersible powders and grains when these are added to water to form a dispersion.

The compositions may also be in the form of liquid preparations to be used as dips or sprays which are generally aqueous dispersions or emulsions containing the active ingredient in the presence of one or more wetting agents, dispersing agents, emulsifying agents or suspending agents.

Wetting agents, dispersing agents and emulsifying agents may be of the cationic, anionic or non-ionic type. Suitable agents of the cationic type include, for example, quaternary ammonium compounds, for example, cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropyl-naphthalene sulphonic acids. Suitable agents of the non-ionic type include, for example, the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins.

Suitable suspending agents are, for example, hydrophilic colloids, for example polyvinylpyrrolidone and sodium carboxymethylcellulose, and the vegetable gums, for example gum acacia and gum tragacanth.

The compositions which are to be used in the form of aqueous dispersions or emulsions are generally supplied in the form of a concentrate containing a high proportion of the active ingredient, the said concentrate to be diluted with water before use. These concentrates are often required to withstand storage for prolonged periods and after such storage to be capable of dilution with water in order to form aqueous preparations which remain homogeneous for a sufficient time to enable them to be applied by conventional spray equipment. The concentrates may conveniently contain from about 10–85% by weight of the active ingredient and generally from about 25–60% by weight of the active ingredient. When diluted to form aqueous preparations, such preparations may contain varying amounts of the active ingredient depending upon the purpose for which they are to be used, but an aqueous preparation containing from between 0.001% and 0.01% up to approximately 10% by weight of active ingredient may be used.

It is to be understood that the biologically active compositions of this invention may comprise, in addition to the diphenylamine derivative of the invention one or more other compounds having biological activity, for example, an insecticide, fungicide or acaricide. They may also incorporate one or more stabilizing agents, for example epoxides, for example epichlorhydrin.

The compositions to be used as sprays may also be in the form of aerosols wherein the formulation is held in a container under pressure in the presence of a propellant such as fluorotrichloromethane or dichlorodifluoromethane.

By the inclusion of suitable additives, for example for improving the distribution, adhesive power and resistance to rain on treated surfaces, the different compositions can be better adapted for the various uses for which they are intended.

The compound and compositions of the invention are useful for combating pests. The term "pest" or "pests" as used in this specification and claims means invertebrate pests, particularly insect and acarine pests, and also foliar fungal pests of plants, and the meaning of "pesticidal" as used herein is similarly limited. In a further aspect therefore, the invention provides a method of combating pests which comprises applying to the pests themselves, to the locus of the pests or to the habitat of the pests the diphenylamine derivative of the present invention or a composition comprising such a diphenylamine derivative. More particularly the invention provides a method of combating pests of plants which comprises applying to the plants the compound or a composition of the present invention. The application may be made to treat an infestation or infection of the plant by the pest which is already occurring, or plants which are liable to such infestation or infection may be treated prophylactically. Application may be of the indiluted chemical in certain instances but it is preferable to apply a composition, such as one of those which have been generally described hereinabove, by dusting or spraying the locus of the pests, for example the foliage of plants. The terms "plant" and "plants" as used herein are intended to mean in general economically useful plants, e.g. food and fibre crop plants or ornamental plants, but of course other types of plant may also be treated at any stage of growth from emergence to maturity, and treatment may be given to the foliage, fruit, stems, trunks or branches of the plants, as appropriate to the particular plant and pest concerned.

The compound of the invention and compositions. comprising it are very toxic to a wide variety of insect and other invertebrate pests, including, for example, the following:

*Tetranychus telarius* (red spider mites)
*Aphis fabae* (aphids)
*Megoura viceae* (aphids)
*Aedes aegypti* (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)

In a preferred aspect the invention provides a method of combating and controlling phytophagous mites which comprises treating plants infested with or liable to infestation by such mites with the diphenylamine derivative of the invention or a composition thereof. Phytophagous mites are economically important pests of many crops, including, for example, cotton, citrus, apples, pears and other top fruit.

The compound and compositions of the invention are also useful in the control of foliar fungal pests of plants, including the following:

*Puccinia recondita* (rust of wheat)
*Plasmopara viticola* (powdery mildew of vines)
*Uncinula necator* (downy mildew of vines)
*Podosphaera leucotricha* (powdery mildew of apples)

Thus it can be seen that the invention provides the opportunity to treat a single crop for both insect and fungal pests of that crop by a single application. For example, the fungal disease *Podosphaera leucotricha* and the mite *Tetranychus telarius* both occur as pests of apple trees, and both may be combated and controlled by application of a composition incorporating the invention compound.

According to a further feature of the invention, therefore, we provide a process for the eradication of undesired insect and fungal infestations in growing plants or crops, which comprises applying to the said infestations in growing plants or crops a sufficient quantity of the diphenylamine derivative of the invention.

It is, of course, well-known in the pesticide art that the application of pesticidally effective materials to plants at rates in excess of the rates necessary to provide an insecticidal, acaricidal or fungicidal effect may cause unwanted damage to the plants. The scope of this invention insofar as it relates to the application of the compound or compositions of the invention to economically useful plants to provide a desirable pesticidal effect does not extend to application of the said compounds or compositions at rates where more than an acceptable level of unwanted damage occurs. The actual rate to be used in any particular circumstance may be readily determined by simple experimentation without the exercise of the inventive faculty and such experimentation is well within the capacity of skilled workers in the art.

Factors to be taken into consideration when determining the correct rate to be used include, the nature of the plant, the nature of the pest, the climatic conditions and the agricultural practice appropriate to the plant and its geographical location. A suitable rate for the treatment of mature apple trees to combat European red spider mite (*Tetranychus telarius*) is from 50 to 250 parts per million of active ingredient in a composition sprayed on at more than 100 liters per hectare.

The invention is illustrated, but not limited, by the following examples:

EXAMPLE 1

This Example illustrates the preparation of 2,5'-bistrifluoromethyl-2'-chloro-4,6-dinitrodiphenylamine.

Powdered potassium hydroxide (60 g) was added in portions over 20 minutes to a stirred solution of 3-amino-4-chloro-benzotrifluoride (97.5 g) in dimethylformamide (750 ml) at the ambient temperature. The mixture was added slowly to 2-chloro-3,5-dinitrobenzotrifluoride (135 g) in dimethylformamide (750 ml) and the resultant mixture stirred at the ambient temperature for 3 hours. This mixture was poured into methylated spirit (5 l) and this solution was acidified with concentrated hydrochloric acid. The precipitate was collected and recrystallised from methylated spirit to yield 2,5'-bistrifluoromethyl-2'-chloro-4,6-dinitrodiphenylamine, melting point 145°–146° C.

EXAMPLE 2

5 Parts by weight of the compound of the invention was thoroughly mixed in a suitable mixer with 95 parts by weight of talc. There was thus obtained a dusting powder.

EXAMPLE 3

10 Parts by weight of the compound of the invention, 10 parts of an ethylene oxide-octyl-phenol condensate ("Lissapol" NX; "Lissapol" is a Trade Mark) and 80 parts by weight of diacetone alcohol were thoroughly mixed. There was thus obtained a concentrate which, on mixing with water, gave an aqueous dispersion suitable for application as a spray in the control of insect pests.

EXAMPLE 4

A granular composition was prepared by dissolving the active ingredient in a solvent, spraying the solution obtained on to the granules of pumice and allowing the solvent to evaporate.

|  | % wt |
|---|---|
| 2,5'-bistrifluoromethyl-2'-chloro-4,6-dinitrodiphenylamine | 5 |
| Pumice granules | 95 |
|  | 100 |

EXAMPLE 5

An aqueous dispersion formulation was prepared by mixing and grinding the ingredient recited below in the proportions stated.

|  | % w |
|---|---|
| 2,5'-bistrifluoromethyl-2'-chloro-4,6-dinitrodiphenylamine | 40 |
| Calcium lignosulphonate | 10 |
| Water | 50 |
|  | 100 |

EXAMPLE 6

An emulsifiable concentrate was made up by mixing together the ingredients set out below in the proportions stated and stirring the mixture until all the constituents were dissolved.

|  | % wt |
|---|---|
| 2,5'-bistrifluoromethyl-2'-chloro-4,6-dinitrodiphenylamine | 10.0 |
| Ethylene Dichloride | 40.0 |
| Calcium dodecylbenzenesulphonate | 5.0 |
| "Lubrol" L | 10.0 |
| "Aromasol" H | 35.0 |
|  | 100.0 |

EXAMPLE 7

A composition in the form of grains readily dispersible in a liquid, e.g. water, was prepared by grinding together the first three of the ingredients listed below in the presence of added water and then mixing in the sodium acetate. The resultant mixture was dried and passed through a British Standard mesh sieve, size 44–100, to obtain the desired size of grains.

|  | % wt |
|---|---|
| 2,5'-bistrifluoromethyl-2'-chloro-4,6-dinitrodiphenylamine | 50.0 |
| "Dispersol" T | 25.0 |
| "Lubrol" APN 5 | 1.5 |
| Sodium acetate | 23.5 |
|  | 100.0 |

EXAMPLE 8

The ingredients listed below were ground together in the proportions stated by weight to produce a powder formulation readily dispersable in liquids

|  | % wt |
|---|---|
| 2,5'-bistrifluoromethyl-2'-chloro-4,6-dinitrodiphenylamine | 45.0 |
| "Dispersol" T | 5.0 |
| "Lissapol" NX | 0.5 |
| "Cellofas" B 600 | 2.0 |
| Sodium acetate | 47.5 |
|  | 100.0 |

EXAMPLE 9

A col formulation (a col formulation is a suspension of finely divided particles in which the mean particle diameter is less than about 3 microns), was prepared by ball-milling the constituents in the amounts set out by weight below, and then forming an aqueous dispersion of the ground mixture with water.

|  | % wt |
|---|---|
| 2,5'-bistrifluoromethyl-2'-chloro-4,6-dinitrodiphenylamine | 40.0 |
| "Dispersol" T | 10.0 |
| "Lubrol" L | 1.0 |
| Water | 49.0 |
|  | 100.0 |

EXAMPLE 10

A dispersible powder formulation was made by mixing together the ingredients in amounts by weight set out below and then grinding the mixture until all the constituents were thoroughly mixed.

|  | % wt |
|---|---|
| 2,5'-bistrifluoromethyl-2'-chloro-4,6-dinitrodiphenylamine | 25.0 |
| "Aerosol" OT/B | 2.0 |
| "Dispersol" AC | 5.0 |
| China clay | 28.0 |
| Silica | 40.0 |
|  | 100.0 |

EXAMPLE 11

This Example illustrates the preparation of two dispersible powder formulations. In each instance all the ingredients are mixed in the proportions (by weight) stated and the mixture then ground in a comminution mill.

|  | % wt |
|---|---|
| 2,5'-bistrifluoromethyl-2'-chloro-4,6-dinitrodiphenylamine | 25.0 |
| "Perminal" BX | 1.0 |
| "Dispersol" T | 5.0 |
| Polyvinylpyrrolidone | 10.0 |
| Silica | 25.0 |
| China clay | 34.0 |

-continued

|  | % wt |
|---|---|
|  | 100.0 |

EXAMPLE 12

The ingredients set out below were formulated into a dispersible powder by mixing and grinding the ingredients in the proportions stated.

|  | % wt |
|---|---|
| 2,5'-bistrifluoromethyl-2'-chloro-4,6-dinitrodiphenylamine | 25.0 |
| "Aerosol" OT/B | 2.0 |
| "Dispersol" AC | 5.0 |
| China clay | 68.0 |
|  | 100.0 |

The following constitutes an explanation of the compositions or substances represented by the various Trade Marks and Trade Names referred to in the foregoing Examples.

| "LUBROL" L | is a condensate of 1 mole of nonyl phenol with 13 molar proportions of ethylene oxide. |
|---|---|
| "AROMASOL" H | is a solvent mixture of alkyl-benzenes. |
| "DISPERSOL" T AND AC | is a mixture of sodium sulphate and a condensate of formaldehyde with the sodium salt of naphthalene sulphonic acid. |
| "LUBROL" APN 5 | is a condensate of 1 mole of nonyl phenol with 5½ moles of naphthalene oxide. |
| "CELLOFAS" B 600 | is a sodium carboxymethyl cellulose thickener. |
| "LISSAPOL" NX | is a condensate of 1 mole of nonyl phenol with 8 moles of ethylene oxide. |
| "AEROSOL" OT/B | is dioctyl sodium sulphosuccinate. |
| "PERMINAL" BX | is an alkyl naphthalene sulphonate (sodium salt). |

"LUBROL", "AROMASOL", "DISPERSOL", "CELLOFAS" and "PERMINAL" are Registered Trade Marks.

EXAMPLE 13

The activity of the diphenylamine derivative of the present invention was shown in tests against a variety of insect and other invertebrate pests. The compound was used in the form of a liquid preparation containing 0.1% by weight of the compound except in the tests with *Aedes aegypti* where the preparations contained 0.01% by weight of the compound in a mixture of solvents consisting of 4 parts by volume of acetone and 1 part by volume of diacetone alcohol. The solutions were then diluted with water containing 0.01% by weight of a wetting agent sold under the trade name "LISSAPOL" NX until the liquid preparations contained the required concentration of the compound. "Lissapol" is a Trade Mark.

The test procedure adopted with regard to each pest was basically the same and comprised supporting a number of pests on a medium which was usually a host plant or a foodstuff on which the pests feed, and treating either or both the pests and the medium with the preparations.

The mortality of the pests was then assessed at periods usually varying from 1 to 3 days after the treatment. The results of the tests are given below in Table I. In this table the first column indicates the name of the pest species. Each of the subsequent columns indicates the host plant or medium on which it was supported, the number of days which were allowed to elapse after the treatment before assessing the mortality of the pests and the result obtained for the compound. The assessment is expressed in integers which range from 0-3.

0 represents less than 30% kill
1 represents 30-49% kill
2 represents 50-90% kill
3 represents over 90% kill In the Table "contact test" indicates that both the pests and the medium were treated, "residual test" indicates that the medium was treated before infestation with the pests.

TABLE I

| PEST SPECIES | SUPPORT MEDIUM | NO. OF DAYS | COMPOUND OF THE INVENTION |
|---|---|---|---|
| *Tetranychus telarius* (red spider mites-adults) | French bean | 3 | 3 |
| *Tetranychus telarius* (red spider mites - eggs) | French bean | 3 | 3 |
| *Aphis fabae* (green aphids) | Broad bean | 2 | 3 |
| *Megoura viceae* (black aphids) | Broad bean | 2 | 3 |
| *Aedes aegypti* (mosquito adults) | Plywood | 1 | 3 |
| *Musca domestica* (houseflies-contact test) | Milk/sugar | 2 | 3 |
| *Musca domestica* (houseflies-residual test) | Plywood | 2 | 0 |
| *Pieris brassicae* (cabbage white caterpillers) contact test | Cabbage | 2 | 3 |
| *Plutella maculipennis* (diamond back moth, larvae, contact test) | Mustard | 2 | 3 |
| *Phaedon cochleariae* (mustard beetles - residual test) | Mustard | 2 | 3 |
| *Aedes aegypti* (mosquito larvae) | Water | 1 | 3 |
| *Dysdercus fasciatus* (capsid) | Grain | 2 | 3 |

EXAMPLE 14

The diphenylamine compound of the invention was tested against a variety of foliar fungal diseases of plants. In the test, a composition comprising an aqueous solution or suspension of the test compound was sprayed on to the foliage of uninfected plants; the soil in which the plants were growing was also drenched with the composition. The compositions used for spraying and drenching contained 50 parts per million (p.p.m.) of the test compound. After spraying and drenching the plants were then exposed to infection with the diseases it was desired to control, along with control plants not treated with the compound. After a period of days, depending upon the particular disease, the extent of the disease was visually assessed, as a percentage of the disease established upon the control plants which had not been treated with the compound under test, according to the grading scheme below:

| GRADING | AMOUNT OF DISEASE AS A PERCENTAGE OF DISEASE ON CONTROL PLANTS |
|---|---|
| 0 | 61 to 100 |
| 1 | 26 to 60 |
| 2 | 6 to 25 |
| 3 | 0 to 5 |
| 4 | No disease |

In Table II below, the names of the diseases are given in the first column, in the second column is given the time which elapsed between exposing the plants to infection and assessing the amount of disease, and in the third column is given the test results.

TABLE II

| DISEASE AND PLANT | TIME INTERVAL (DAYS) | GRADING |
|---|---|---|
| *Puccinia recondita* (wheat) | 10 | 2 |
| *Podosphaera leucotricha* (apple) | 10 | 4 |
| *Plasmopara viticola* (vine) | 7 | 4 |
| *Uncinula necator* (vine) | 10 | 4 |

EXAMPLE 15

This Example illustrates the favourable level of control of both organo-phosphorus susceptible and resistant strains of the European red-spider mite *Tetranychus telarius* by the diphenylamine compound of the invention (hereinafter referred to as Compound A) in comparison with compounds disclosed in U.S. Application Ser. No. 556,421, some of which are very toxic to mammals.

French bean plants at the primary leaf stage infested with red-spider mites *Tetranychus telarius* were sprayed with compositions comprising the active compounds at a variety of rates. Table III gives the lowest rate of application sufficient to give complete control, 3 days after application, of the red-spider mites. Table III also gives the toxicity of the compounds towards female rats.

It can be seen from Table III that Compound A is one of only three compounds having favourable mammalian toxicity and to give favourable control of *Tetranychus telarius,* the other two compounds being numbers 3 and 5 of Table III.

TABLE III

COMPOUND:

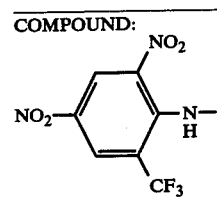

| COMPOUND NO. | RATE OF APPLICATION (p.p.m.)* | L.D. 50 (mg/kg)+ |
|---|---|---|
| A | 10 | 100 |
| 1  | 50 | <10 |
| 2 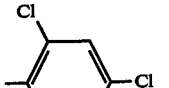 | 5 | <10 |
| 3 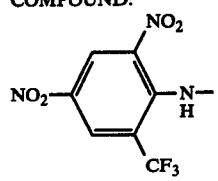 | 2.5 | 200 |
| 4 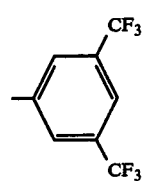 | 10 | <10 |
| 5 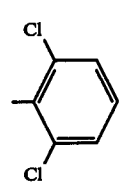 | 2.5 | 150 |
| 6 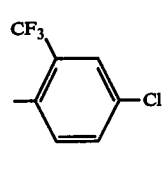 | 2.5 | 1.7 |
| 7 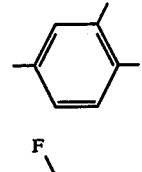 | 10 | 10–50 |
| 8 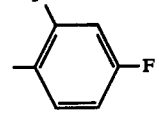 | 25 | 100–500 |
| 9 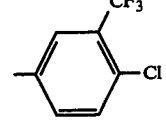 | 5 | <10 |
| 10 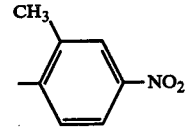 | 100 | — |
| 11 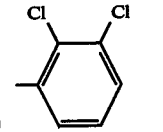 | 50 | — |
| 12  | 100 | — |

TABLE III-continued

COMPOUND:

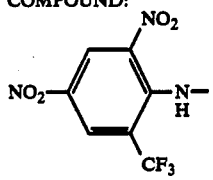

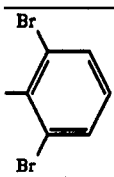

| COMPOUND NO. | RATE OF APPLICATION (p.p.m.)* | L.D. 50 (mg/kg)+ |
|---|---|---|
| 13 | 10 | 50 |

*Lowest rate of application to give 100% kill of *Tetranychus telarius*, Adults and Eggs (p.p.m.)

+L.D. 50 values (female rat) oral administration milligrams compound per kilogram of live body weight.

EXAMPLE 16

This Example illustrates, in several tests, the favourable level of control of the adult female aphid Myzus persicae by Compound A the compound of the invention in comparison with the two compounds disclosed in U.S. application Ser. No. 556,421 which have as given in Table III similar acaricidal activity and mammalian toxicity. The results of this test are given in Tables IV–VI along with the results for "METASYSTOX", a compound recommended for the control of aphids. "METASYSTOX" is a Trade Mark.

Test 1. Adult female *M. persicae* were sprayed under a modified Potter Tower. The aphids were sprayed on Chinese cabbage leaf. 4 Mls solution at 10 lbs per square inch pressure delivered per replica. After spraying, the aphids were confined in open fluon-treated glass rings.

In tests IV and VI Compound A was markedly more active to aphids than were Compound nos 3 and 5, whilst in test V only Compound no 3 approached a similar level of activity as that attained by Compound A.

TABLE IV:

| | TREATED APHIDS ON TREATED LEAVES | | | | |
|---|---|---|---|---|---|
| | COMPOUND | RATE ppm. | 21 HOUR ASSESSMENT | | |
| TREATMENT | NO. (TABLE III) | ACTIVE INGREDIENT | DEAD | % AFFECTED | HEALTHY |
| ![structure with CF3, Cl, O2N, NO2, Cl] | 3 | 200 | 52 | 28 | 20 |
| | | 100 | 62 | 28 | 10 |
| | | 50 | 47 | 22 | 31 |
| ![structure with CF3, Cl, O2N, NO2, Cl] | 5 | 200 | 68 | 26 | 6 |
| | | 100 | 53 | 40 | 7 |
| | | 50 | 53 | 27 | 20 |
| Compound A | — | 200 | 87 | 13 | 0 |
| | | 100 | 87 | 13 | 0 |
| | | 50 | 73 | 24 | 3 |
| Metasystox | — | 200 | 100 | 0 | 0 |
| | | 100 | 100 | 0 | 0 |
| | | 50 | 100 | 0 | 0 |
| CONTROL | — | — | 14 | 0 | 86 |

Test 2. *Myzus persicae* on Chinese cabbage sprayed contact under the modified Potter Tower. 4 Ml per replica, 10 lbs per square inch pressure. When sprayed, the aphids were transferred to unsprayed Chinese cabbage leaf and confined in open-ended fluon-treated glass rings. Results are given in Table V.

TABLE V:

| | TREATED APHIDS ON UNTREATED LEAVES | | | | |
|---|---|---|---|---|---|
| | COMPOUND | RATE ppm. | 21 HOUR ASSESSMENT | | |
| TREATMENT | NO. (TABLE III) | ACTIVE INGREDIENT | DEAD | % AFFECTED | HEALTHY |
| ![structure with CF3, Cl, O2N, NO2, Cl] | 3 | 100 | 20 | 13 | 67 |

TABLE V:-continued

| TREATED APHIDS ON UNTREATED LEAVES | | | | | |
|---|---|---|---|---|---|
| | COMPOUND | RATE ppm. | 21 HOUR ASSESSMENT | | |
| TREATMENT | NO. (TABLE III) | ACTIVE INGREDIENT | DEAD | % AFFECTED | HEALTHY |
| [structure: $O_2N$-phenyl ring with $CF_3$, $NO_2$ substituents, -NH- linker, second phenyl with 2,6-Cl] | 5 | 100 | 0 | 14 | 86 |
| Compound A | — | 100 | 21 | 0 | 79 |
| Metasystox | — | 100 | 69 | 6 | 25 |
| CONTROL | — | — | 6 | 0 | 94 |

Test 3. Pieces of Chinese cabbage were sprayed under the modified Potter Tower as above. Almost immediately - when the leaf was still wet, untreated *Myzus persicae* were transferred to the treated leaf. Aphids were confined in open-ended, fluon-treated glass rings. Results are given in Table VI.

much too phytotoxic to the host plants to be of any further interest and was therefore not included in these trials.

In the trials fruiting apple trees were usually sprayed at high volume (i.e. greater than 100 liters/hectare), with various formulations. The leaves of the trees were

TABLE VI:

| UNTREATED APHIDS ON TREATED LEAVES | | | | | |
|---|---|---|---|---|---|
| | COMPOUND | RATE ppm | 21 HOUR ASSESSMENT | | |
| TREATMENT | NO. (TABLE III) | ACTIVE INGREDIENT | DEAD | % AFFECTED | HEALTHY |
| [structure: $O_2N$-phenyl with $CF_3$, $NO_2$, -NH-, second phenyl with 2,5-Cl] | 3 | 100 | 19 | 0 | 81 |
| [structure: $O_2N$-phenyl with $CF_3$, $NO_2$, -NH-, second phenyl with 2,6-Cl] | 5 | 100 | 20 | 7 | 73 |
| Compound A | — | 100 | 27 | 33 | 40 |
| Metasystox | — | 100 | 100 | 0 | 0 |
| CONTROL | — | — | 0 | 0 | 100 |

EXAMPLE 17

Series of field experiments were carried out in several countries throughout the World to compare the acaricidal efficaciousness of the compound of the invention with that of the compound with the most favourable biological properties of U.S. application Ser. No. 556,421 i.e. Compound 3 of Table III. In preliminary trials Compound 5 of that Table III was shown to be then inspected at intervals and the population of the phytophagous mites assessed. For the purpose of comparison the commercial product tricyclohexyltin hydroxide (sold under the Trade Mark "PLICTRAN") was included in the trials. "Plictran" is a recommended treatment for the control of phytophagous mites.

In all the trials no unfavourable phytotoxicity or damage to the fruit was obtained.

| FIELD EXPERIMENT NO. 1. WACHENHEIM, WEST GERMANY, 1975 TRIAL 7532A-IV-4. APPLE:-JAMES GRIEVE | | | | | | | |
|---|---|---|---|---|---|---|---|
| POPULATION OF SPIDER MITES PER 40 LEAVES | | | | | | | |
| | | RATE OF APPLICATION | DAYS AFTER TREATMENT BEFORE ASSESSMENT | | | | |
| TREATMENT | FORMULATION | p.p.m. (a.i.)* | PRE-SPRAY | 5 | 11 | 18 | 25 |
| Control | — | — | 4302 | 4859 | 5371 | 5322 | 3711 |
| Compound No. 3 (Table III | Dispersible Grain | 125 | 3172 | 895 | 1302 | 859 | 230 |
| | | 250 | 1749 | 1009 | 591 | 407 | 56 |
| | | 500 | 2975 | 889 | 400 | 151 | 9 |
| Compound A | Dispersible Grain | 62.5 | 2037 | 446 | 277 | 360 | 11 |
| | | 125 | 3974 | 329 | 53 | 45 | 2 |
| | | 250 | 3400 | 301 | 34 | 55 | 16 |

FIELD EXPERIMENT NO. 1. WACHENHEIM, WEST GERMANY, 1975
TRIAL 7532A-IV-4. APPLE:-JAMES GRIEVE

POPULATION OF SPIDER MITES PER 40 LEAVES

| TREATMENT | FORMULATION | RATE OF APPLICATION p.p.m. (a.i.)* | DAYS AFTER TREATMENT BEFORE ASSESSMENT | | | | |
|---|---|---|---|---|---|---|---|
| | | | PRE-SPRAY | 5 | 11 | 18 | 25 |
| Plictran | Wet Powder | 250 | 2542 | 1035 | 1125 | 560 | 85 |

*"a.i." denotes "active ingredient"

FIELD EXPERIMENT NO. 2. WACHENHEIM, WEST GERMANY, 1975.
TRIAL 7532A-IV-2. APPLE:-GOLDPARMAENE.

% KILL OF SPIDER MITES PER 40 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | | |
|---|---|---|---|---|---|---|---|
| | | | | 6 | 13 | 21 | 28 |
| Control | — | — | 2394 | 0 | 0 | 0 | 0 |
| Compound No. 3 (Table III) | Dispersible Grain | 125 | 1552 | 51.3 | 42.1 | 56.6 | 50.0 |
| | | 250 | 1450 | 80.2 | 74.7 | 86.0 | 68.1 |
| | | 500 | 2115 | 57.1 | 59.7 | 67.1 | 53.6 |
| Compound A | Dispersible Grain | 62.5 | 2774 | 92.2 | 93.5 | 95.4 | 91.0 |
| | | 125 | 3074 | 93.5 | 96.2 | 97.3 | 95.5 |
| | | 250 | 2036 | 90.4 | 93.6 | 96.1 | 91.8 |
| Plictran | Wet Powder | 250 | 2669 | 77.4 | 92.8 | 96.9 | 87.5 |

FIELD EXPERIMENT NO. 3. WACHENHEIM, WEST GERMANY, 1975.
TRIAL 7532A-IV-3. APPLE:-GOLDEN DELICIOUS.

% KILL OF SPIDER MITES PER 40 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | | |
|---|---|---|---|---|---|---|---|
| | | | | 6 | 14 | 21 | 32 |
| Control | — | — | 1022 | 0 | 0 | 0 | 0 |
| Compound No. 3 (Table III) | Dispersible Grain | 125 | 2097 | 79.6 | 93.6 | 83.0 | 87.7 |
| | | 250 | 1155 | 26.2 | 94.9 | 75.2 | 88.7 |
| | | 500 | 1091 | 61.2 | 91.4 | 72.6 | 88.5 |
| Compound A | Dispersible Grain | 62.5 | 1371 | 85.1 | 98.0 | 81.3 | 93.6 |
| | | 125 | 1276 | 82.7 | 98.3 | 83.5 | 93.5 |
| | | 250 | 1282 | 79.1 | 99.7 | 92.9 | 98.4 |
| Plictran | Wet Powder | 250 | 1255 | 81.5 | 97.5 | 83.4 | 87.3 |

FIELD EXPERIMENT NO. 4. HEIDELBERG, WEST GERMANY, 1975.
TRIAL 7532A-IV-1. APPLE:-GOLDEN DELICIOUS.

% KILL OF SPIDER MITES PER 40 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | |
|---|---|---|---|---|---|---|
| | | | | 6 | 13 | 20 |
| Control | — | — | 1767 | 0 | 0 | 0 |
| Compound No. 3 (Table III) | Dispersible Grain | 125 | 1277 | 43.5 | 29.2 | 19.3 |
| | | 250 | 1479 | 81.4 | 76.9 | 57.5 |
| | | 500 | 1643 | 92.6 | 88.1 | 77.5 |
| Compound A | Dispersible Grain | 62.5 | 1135 | 79.8 | 64.8 | 42.5 |
| | | 125 | 844 | 90.0 | 81.6 | 32.5 |
| | | 250 | 1130 | 95.6 | 95.0 | 75.4 |
| Plictran | Wet Powder | 250 | 748 | 0 | 0 | 11.4 |

FIELD EXPERIMENT NO. 5. MONSERRAT, SPAIN, 1975.
TRIAL ES1-75-037. APPLE:- 4 YRS OLD GOLDEN DELICIOUS AND STARKING

% KILL OF SPIDER MITES PER 40 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | |
|---|---|---|---|---|---|---|
| | | | | 5 | 12 | 20 |
| Control | — | — | 2624 | 36.0 | 44.8 | 74.6 |
| Compound No. 3 | Col | 100 | 3538 | 97.0 | 99.0 | 96.8 |

FIELD EXPERIMENT NO. 5. MONSERRAT, SPAIN, 1975.
TRIAL ES1-75-037. APPLE:- 4 YRS OLD GOLDEN DELICIOUS AND STARKING
% KILL OF SPIDER MITES PER 40 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | |
|---|---|---|---|---|---|---|
| | | | | 5 | 12 | 20 |
| (Table III) | | 200 | 2492 | 97.7 | 97.1 | 88.7 |
| Compound A | Col | 100 | 2385 | 97.4 | 98.9 | 98.1 |
| | | 200 | 2926 | 99.2 | 99.3 | 97.9 |
| Plictran | | 100 | 3278 | 80.8 | 86.5 | 93.3 |
| | | 200 | 3090 | 68.0 | 69.6 | 84.3 |
| | | 300 | 3485 | 93.6 | 95.7 | 96.4 |

FIELD EXPERIMENT NO. 6. MONSERRAT, SPAIN, 1975.
TRIAL ES1-74-002. APPLE:-4 YRS OLD GOLDEN DELICIOUS AND STARKING
POPULATION OF SPIDER MITES PER 30 LEAVES

| TREATMENT | FORMULATION | RATE OF APPLICATION p.p.m. (a.i.) | POPULATION PRE-SPRAY | DAYS AFTER TREATMENT BEFORE ASSESSMENT | | | |
|---|---|---|---|---|---|---|---|
| | | | | 4 | 10 | 22 | 28 |
| Control | — | — | 2762 | 1434 | 2270 | 1488 | 712 |
| Compound No. 3 | Col | 100 | 1964 | 96 | 930 | * | * |
| (Table III) | | 200 | 2140 | 35 | 177 | 76 | 112 |
| | | 300 | 1947 | 59 | 422 | 93 | 101 |
| Compound A | Col | 100 | 2396 | 99 | 214 | 172 | 277 |
| | | 200 | 2121 | 48 | 67 | 109 | 146 |
| | | 300 | 1174 | 9 | 61 | 38 | 81 |
| Plictran | Wet Powder | 250 | 2374 | 304 | 530 | 685 | 648 |

*Further spray needed to control spider mite infestation.

FIELD EXPERIMENT NO. 7. FERRARA, ITALY, 1975.
TRIAL EI1-75101. APPLE:-IMPERATOR AND STAR CRIMSON
% REDUCTION IN SPIDER MITE POPULATION PER 40 LEAVES (10 LEAVES PER TREE)

| TREATMENT | FORMULATION | RATE OF APPLICATION p.p.m. (a.i.) | POPULATION PRE-SPRAY | DAYS AFTER TREATMENT BEFORE ASSESSMENT | | | |
|---|---|---|---|---|---|---|---|
| | | | | 8 | 16 | 23 | 30 |
| Control | — | — | 1078 | 0 | 0 | 0 | 0 |
| Compound No. 3 (Table III) | Dispersible Grain | 150 | 1266 | 84.6 | 96.2 | 97.1 | 67.4 |
| | Col | 150 | 932 | 92.1 | 95.6 | 97.8 | 77.8 |
| Compound A | Dispersible Grain | 100 | 1105 | 96.8 | 99.2 | 98.6 | 86.0 |
| | Col | 100 | 908 | 95.6 | 98.9 | 98.3 | 86.0 |
| Plictran | Wet Powder | 200 | 998 | 45.7 | 96.8 | 93.2 | 38.2 |

FIELD EXPERIMENT NO. 8. ARGENTINA, 1974-5.
Three trials conducted by Ing. J D Vermuelen INTA General Roca. Report contributed by Ing. R O Piterbarg. Duperial Buenos Aires. *Panonychus ulmi* on Apple. Number of mobile mites per leaf.

| TREATMENT | FORMULATION | RATE OF APPLICATION p.p.m. (a.i.) | DAYS AFTER TREATMENT | | |
|---|---|---|---|---|---|
| | | | 21 | 29 | 41 |
| TRIAL ARG1 | | | | | |
| Control | — | | 115.3 | 197.8 | 108.1 |
| Compound No. 3 (Table III) | Dispersible Grain | 70 | 1.7 | 19.7 | 34.5 |
| Compound A | Dispersible Grain | 50 | 0.6 | 5.0 | 37.7 |
| Plictran | Wet Powder | 200 | 1.4 | 2.3 | 13.0 |
| TRIAL ARG2 | | | | | |
| Control | — | — | 73.8 | 151.4 | 91.0 |
| Compound No. 3 (Table III) | Dispersible Grain | 140 | 1.2 | 3.6 | 16.9 |
| Compound A | Dispersible Grain | 100 | 0.7 | 2.2 | 8.4 |
| Plictran | Wet Powder | 200 | 0.8 | 1.1 | 6.4 |
| TRIAL ARG3 | | | | | |
| Control | — | — | 81.1 | 124.8 | 177.4 |
| Compound No. 3 | Dispersible | 280 | 0.8 | 4.3 | 28.4 |

-continued
FIELD EXPERIMENT NO. 8. ARGENTINA, 1974-5.
Three trials conducted by Ing. J D Vermuelen INTA General Roca. Report contributed by Ing. R O Piterbarg. Duperial Buenos Aires. *Panonychus ulmi* on Apple. Number of mobile mites per leaf.

| TREATMENT | FORMULATION | RATE OF APPLICATION p.p.m. (a.i.) | DAYS AFTER TREATMENT 21 | 29 | 41 |
|---|---|---|---|---|---|
| (Table III) Compound A | Grain Dispersible Grain | 200 | 0.0 | 1.5 | 7.0 |
| Plictran | Wet Powder | 200 | 0.5 | 1.1 | 20.8 |

FIELD EXPERIMENT NO. 9. SOUTH AFRICA
Trials conducted by and report contributed by D Joubert/J Heyns Triomf Pty. Somerset West, Cape Province. Trials 1–4 Red Spider (*T. cinnabarinus*). Trial 5 European red mite.

Trial SAF 1. Apple variety Star King

| TREATMENT | GRAMS PER 100 LITERS | P.P.M. (a.i.) | PRE SPRAY MITE NUMBERS | MOBILE MITES PER LEAF.. DAYS AFTER SPRAYING 7 | 21 | 28 | 35 |
|---|---|---|---|---|---|---|---|
| Control | — | — | 116 | 87 | 203 | sprayed out | |
| Plictran 25 Wettable Powder | 140 | 350 | 110 | 8 | 35 | sprayed out | |
| Compound No. 3 (Table III) | 50 | 175 | 127 | 8 | 33 | sprayed out | |
| | 100 | 350 | 120 | 14 | 35 | sprayed out | |
| | 150 | 525 | 115 | 3 | 18 | 25 | 20 |
| Compound A | 25 | 125 | 119 | 2 | 12 | 36 | 37 |
| | 50 | 250 | 112 | 5 | 13 | 29 | 25 |
| | 100 | 500 | 132 | 6 | 13 | 21 | 25 |

(Trial SAF 2). Apple variety Star King

| TREATMENT | GRAMS PER 100 LITRES | P.P.M. (a.i.) | PRE SPRAY MITE NUMBERS | MOBILE MITES PER LEAF.. DAYS AFTER SPRAYING 7 | 21 | 28 | 35 | 42 |
|---|---|---|---|---|---|---|---|---|
| Control | — | — | 79 | 123 | 247 | 218 | 231 | sprayed out |
| Plictran 25 WP | 140 | 350 | 73 | 4 | 3 | 5 | 9 | 2 |
| Compound No. 3 (Table III) | 50 | 175 | 67 | 16 | 29 | 21 | 30 | 16 |
| | 100 | 350 | 68 | 23 | 25 | 39 | 39 | sprayed out |
| Compound A | 50 | 250 | 66 | 9 | 12 | 5 | 7 | 5 |
| | 100 | 500 | 89 | 6 | 6 | 5 | 9 | 7 |

Trial SAF 3. Apple variety's Star King and Golden Delicious

| TREATMENT | GRAMS PER 100 LITERS | P.P.M. (a.i.) | PRE SPRAY MITE NUMBERS | MOBILE MITES PER LEAF.. DAYS AFTER SPRAYING 7 | 21 | 28 | 35 | 42 |
|---|---|---|---|---|---|---|---|---|
| Control | — | — | 84 | 22 | 381 | | sprayed out | |
| Plictran 25 WP | 140 | 350 | 80 | 2 | 16 | 57 | sprayed out | |
| Compound No. 3 Table (III) | 50 | 175 | 86 | 0 | 18 | 41 | sprayed out | |
| | 75 | 263 | 84 | 1 | 5 | 25 | 33 | 28 |
| | 100 | 350 | 80 | 2 | 4 | 18 | 20 | 21 |
| Compound A | 50 | 250 | 77 | 2 | 4 | 9 | 26 | 19 |
| | 75 | 375 | 76 | 3 | 2 | 4 | 11 | 3 |
| | 100 | 500 | 95 | 0 | 3 | 18 | 20 | 27 |

Trial SAF 4. Apple variety Ohenimuri

| TREATMENT | GRAMS PER 100 LITERS | P.P.M. (a.i.) | PRE SPRAY MITE NUMBERS | MOBILE MITES PER LEAF.. DAYS AFTER SPRAYING 7 | 21 | 28 | 35 | 42 |
|---|---|---|---|---|---|---|---|---|
| Control | — | — | 98 | 117 | | sprayed out | | |
| Plictran 25 WP | 140 | 350 | 73 | 4 | 1 | 21 | 18 | 50 |
| Compound No. 3 Table (III) | 50 | 175 | 85 | 15 | 12 | 65 | 131 | 132 |
| | 100 | 350 | 73 | 23 | 13 | 38 | 30 | 64 |
| Compound A | 50 | 250 | 74 | 2 | 0 | 6 | 5 | 22 |
| | 100 | 500 | 82 | 4 | 1 | 2 | 2 | 10 |

Trial SAF 5. Apple variety Star King

| TREATMENT | GRAMS PER 100 LITERS | P.P.M. (a.i.) | PRE SPRAY MITE NUMBERS | MOBILE MITES PER LEAF.. DAYS AFTER SPRAYING 7 | 21 | 28 | 35 | 42 |
|---|---|---|---|---|---|---|---|---|
| Control | — | — | 464 | 260 | 492 | | sprayed out | |
| Plictran 25 WP | 140 | 350 | 478 | 0 | 0 | 2 | 4 | 16 |

| | | | -continued | | | | | |
|---|---|---|---|---|---|---|---|---|
| Compound No. 3 | 50 | 175 | 324 | 0 | 0 | 9 | 19 | 56 |
| Table (III) | 100 | 350 | 308 | 0 | 0 | 11 | 28 | 5 |
| Compound A | 50 | 250 | 249 | 0 | 0 | 7 | 28 | 21 |
| | 100 | 500 | 421 | 0 | 0 | 1 | 4 | 4 |

We claim:

1. 2,5'-Bistrifluoromethyl-2'-chloro-4,6-dinitrodiphenylamine having the formula:

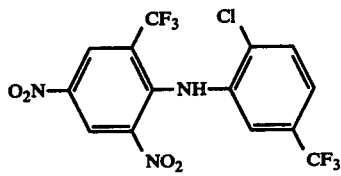

2. Pesticidal compositions comprising as an active ingredient a pesticidally effective amount of the diphenylamine derivative as claimed in claim 1, in association with a diluent or carrier.

3. Pesticidal composition as claimed in claim 2 wherein the diluent or carrier is a solid diluent or carrier in powder or granule form.

4. Pesticidal composition as claimed in claim 2 wherein the diluent or carrier is a liquid diluent or carrier.

5. Pesticidal compositions as claimed in claim 2 comprising a wetting, dispersing or emulsifying agent.

6. Pesticidal compositions as claimed in claim 2 comprising at least one other pesticidally active ingredient selected from the group consisting of an insecticide, acaricide and fungicide.